US008530187B2

(12) United States Patent
Caligiuri et al.

(10) Patent No.: US 8,530,187 B2
(45) Date of Patent: Sep. 10, 2013

(54) METHODS FOR TRANSFECTING NATURAL KILLER CELLS

(75) Inventors: Michael A. Caligiuri, Columbus, OH (US); Rossana Trotta, Dublin, OH (US); Jianhua Yu, Columbus, OH (US); Brian Becknell, Westerville, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 743 days.

(21) Appl. No.: 10/599,194

(22) PCT Filed: Mar. 21, 2005

(86) PCT No.: PCT/US2005/009238
§ 371 (c)(1),
(2), (4) Date: Aug. 20, 2008

(87) PCT Pub. No.: WO2005/093079
PCT Pub. Date: Oct. 6, 2005

(65) Prior Publication Data
US 2008/0299660 A1    Dec. 4, 2008

Related U.S. Application Data

(60) Provisional application No. 60/555,177, filed on Mar. 22, 2004.

(51) Int. Cl.
C12P 21/02    (2006.01)
(52) U.S. Cl.
USPC ............ 435/69.1; 435/372.3; 435/320.1; 435/235.1
(58) Field of Classification Search
None
See application file for complete search history.

(56) References Cited

U.S. PATENT DOCUMENTS

| 2003/0104384 A1 | 6/2003 | Nolan et al. | |
| 2005/0113564 A1* | 5/2005 | Campana et al. | 530/350 |
| 2007/0014785 A1* | 1/2007 | Golay et al. | 424/131.1 |

OTHER PUBLICATIONS

Fischer et al., Exp. Clin. Cardiol. vol. 7, pp. 106-112 (2002).*
Kingston et al., Current Protocols in Molecular Biology (1996) pp. 9.1.1-9.1.11.*
First examination report of the European Patent Office for European patent application No. 05 732 514.4-2401 dated Oct. 7, 2008.
Second Exam report for European patent application No. 05732514.4-2401—Dated Jan. 13, 2010—(3 pages).
Third Exam report for European patent application No. 05732514.4-2403—Dated Mar. 8, 2011—(4 pages).
Chiorean, et al. "BCR/ABL alters the function of NK cells and the acquisition of killer immunoglobulinlike receptors (KIRs)", Blood, (May 1, 2003), vol. 101, No. 9, pp. 3527-3533.
Fehniger, et al. "Ontogeny and expansion of human natural killer cells: clinical implications", Int. Rev. Immunol., (2001), vol. 20, No. 3-4, pp. 503-536.
Fehniger, et al. "Interleukin-2 and interleukin-15: immunotherapy for cancer", Cytokine Growth Factor Rev., (Apr. 2002), vol. 13, No. 2, pp. 169-183.
Galandrini, et al. "The adaptor protein shc is involved in the negative regulation of NK cell-mediated cytotoxicity", Eur. J. Immunol., (Jul. 2001), vol. 31, No. 7, pp. 2016-2025.
Introna, et al. "Rapid retroviral infection of human haemopoietic cells of different lineages: efficient transfer in fresh T cells", Br. J. Haematol., (Nov. 1998), vol. 103, No. 2, pp. 449-461.
Jiang, et al. "Pivotal role of phosphoinositide-3 kinase in regulation of cytotoxicity in natural killer cells", Nature Immunology, (Nov. 2000) vol. 1, No. 5, pp. 419-425.
Kikuchi-Maki, et al. "KIR2DL4 is an IL-2-regulated NK cell receptor that exhibits limited expression in humans but triggers strong IFN-gamma production", The Journal of Immunology, (Oct. 1, 2003), vol. 171, No. 7, pp. 3415-3425.
Kinoshita, et al. "The T cell activation factor NF-Atc positively regulates HIV-1 replication and gene expression of T cells", Immunity, (Mar. 1997), vol. 6, pp. 235-244.
Kinsella, et al. "Episomal vectors rapidly and stably produce high-titer recombinant retrovirus", Human Gene Therapy, (Aug. 1, 1996), vol. 7, pp. 1405-1413.
Lieberman, et al. "Regulatory pathways involved in the infection-induced production of IFN-gamma by NK cells", Microbes and Infection, (Dec. 2002) vol. 4, No. 15, pp. 1531-1538.
Maasho, et al. "Efficient gene transfer into the human natural killer cell line, NKL, using the Amaxa nucleofection system", J. Immunol. Methods, (Jan. 2004), vol. 284, No. 1-2, pp. 133-140.
Palu, et al. "Progress with retroviral gene vectors", Rev. Med. Virol., (May-Jun. 2000), vol. 10, No. 3, pp. 185-202.
Ruggeri, et al. "Effectiveness of donor natural killer cell alloreactivity in mismatched hematopoietic transplants", Science, (Mar. 15, 2002), vol. 295, pp. 2097-2100.
Schroers, et al. "Gene transfer into human T lymphocytes and natural killer cells by Ad5/F35 chimeric adenoviral vectors", Exp. Hematol., (Jun. 2004), vol. 32, No. 6, pp. 536-546.
Shankaran, et al. "IFNgamma and lymphocytes prevent primary tumor development and shape tumor immunogenicity", Nature, (Apr. 26, 2001), vol. 410, pp. 1107-1111.
Trompeter, et al. "Rapid and highly efficient gene transfer into natural killer cells by nucleofection", Journal of Immunological Methods, (Mar. 1, 2003), vol. 274, pp. 245-256.
Trotta, et al. "Differential Expression of SHIP1 in CD56(bright) and CD56(dim) NK cells provides a molecular basis for distinct functional responses to monokine costimulation", Blood (1st ed. Paper), prepublished online Dec. 16, 2004, pp. 1-34.
Unutmaz, et al. "Cytokine signals are sufficient for HIV-1 infection of resting human T lymphocytes", Journal of Experimental Medicine, (Jun. 7, 1999), vol. 189, No. 11, pp. 1735-1746.
Windebank, et al. "Signal transduction during human natural killer cell activation: inositol phosphate generation and regulation by cyclic AMP", The Journal of Immunology, (Dec. 1, 1988), vol. 141, No. 11, pp. 3951-3957.

(Continued)

Primary Examiner — Jim Ketter
(74) Attorney, Agent, or Firm — Calfee, Halter & Griswold

(57) ABSTRACT

Methods for stably transfecting mammalian natural killer cells comprising: transfecting a packaging cell line with a retroviral expression vector; culturing the transfected packaging cell line in a cell culture medium; and culturing the mammalian natural killer cells with the cell culture medium. Natural killer cells transfected according to the disclosed methods are also provided.

10 Claims, 9 Drawing Sheets

(56) References Cited

OTHER PUBLICATIONS

Yusa, et al. "SHP-1-and phosphotyrosine-independent inhibitory signaling by a killer cell Ig-like receptor cytoplasmic domain in human NK cells", The Journal of Immunology, (May 15, 2002), vol. 168, pp. 5047-5057.
Sharifi, et al. "NK Cells as New Target for Gene Therapy; Using Retroviral Vectors as Promising Delivery System", Blood, (Nov. 16, 2002), vol. 100, No. 11, Abstract No. 2559: 44TH Annual Meeting of the American Society of Hematology; Philadephia, PA, USA; ISSN: 0006-4971 (abstract only).
Levy, et al. Virology, (1994), 3d ed., pp. 129-133 and pp. 189-191.
International Search Report for PCT/US05/009238, issued Aug. 9, 2005 (1 page).
Office Action for Canadian Patent Application No. 2,560,751 dated Jun. 19, 2012.
PCT US2005/009238—Written Opinion mailed on Aug. 9, 2005 (4 pages).
PCT US2005/009238—IPRP issued on Sep. 26, 2006 (4 pages).
EP 05732514.4—Supplementary European Search Report mailed Mar. 9, 2007 (3 pages).
Becknell et al., "Efficient infection of human natural killer cells with an EBV/retroviral hybrid vector", Journal of Immunological Methods (2005), vol. 296, No. 1-2, pp. 115-123 (Epub. Dec. 8, 2004).
Carson et al., "Interleukin (IL) 15 Is a Novel Cytokine That Activates Human Natural Killer Cells via Components of the IL-2 Receptor", J. Exp. Med. (Oct. 1994), vol. 180, No. 4, pp. 1395-1403.
Cheng et al., "Report on design and construction of recombinantretrovirus vector expressing siRNA for survivin geneknockdown", Shiyong Zhongllu Zazhi (2005), vol. 20, No. 2, pp. 128-133 (Abstract Only).
Cooper et al., "Human natural killer cells: a unique innate immunoregulatory role for the CD56(bright) subset", Blood (May 15, 2001), vol. 97, No. 10, pp. 3146-3151.
Grignani et al., "High-Efficiency Gene Transfer and Selection of Human Hematopoietic Progenitor Cells with a Hybrid EBV/Retroviral Vector Expressing the Green Fluorescence Protein", Cancer Research (Jan. 1, 1998), vol. 58, No. 1, pp. 14-19.
Isobe et al., "Epstein-Barr Virus Infection of Human Natural Killer Cell Lines and Peripheral Blood Natural Killer Cells", Cancer Research (Mar. 15, 2004), vol. 64, No. 6, pp. 2167-2174.
Liberatore et al., "Natural Killer Cell-mediated Lysis of Autologous Cells Modified by Gene Therapy", J. Exp. Med. (Jun. 21, 1999), vol. 189, No. 12, pp. 1855-1862.
Nagashima et al., "Stable Transduction of the Interleukin-2 Gene Into Human Natural Killer Cell Lines and Their Phenotypic and Functional Characterization In Vitro and In Vivo", Blood (May 15, 1998), vol. 91, No. 10, pp. 3850-3861.
Sattler et al., "BCR/ABL Directly Inhibits Expression of SHIP, an SH2-Containing Polyinosito1-5-Phosphatase Involved in the Regulation of Hematopoiesis", Mole. Cell. Biol. (Nov. 1999), vol. 19, No. 11, pp. 7473-7480.
Strengell et al., "IL-21 in Synergy with IL-15 or IL-18 Enhances IFN-gamma Production in Human NK and T Cells", The Journal of Immunology (Jun. 2003), vol. 170, No. 11, pp. 5464-5469.
Trotta et al., "BCR/ABL activates mdm2 mRNA translation via the La antigen", Cancer Cell (Feb. 2003), vol. 3, No. 2, pp. 145-160.

\* cited by examiner

METHODS FOR TRANSFECTING NATURAL KILLER CELLS

This application claims priority to U.S. Provisional Application No. 60/555,177, filed Mar. 22, 2004, the entire disclosure of which is incorporated herein by reference.

Research leading to the present invention was funded, at least in part, by NIH Grant Nos. P0ICA95426 and R01CA68458. The government has certain rights in this invention.

DESCRIPTION OF THE INVENTION

1. Field of the Invention

The invention generally relates to methods for transfecting eukaryotic cells, such as primary natural killer (NK) cells. The methods involve the use of an EBV/retroviral expression vector, such as PINCO, and a packaging cell line, such as Phoenix cells.

2. Background of the Invention

The innate immune system represents the human body's essential first line of defense against cancer as well as infectious disease. In the immune competent host, innate immune effectors act rapidly to restrict the dissemination of disease, as well as to trigger the adaptive, or antigen-specific, immune system. Natural killer (NK) cells are CD56$^+$CD3$^-$ large granular lymphocytes that constitute one component of the innate immune system. In addition to their potent cytolytic activity, NK cells elaborate a host of immunoregulatory cytokines and chemokines, which play a crucial role in pathogen clearance. In particular, NK cells produce nanogram quantities of gamma interferon (IFN-γ), a critical cytokine for the clearance of infectious pathogens as well as for tumor surveillance.

In rodent models, NK cells have been proven effective for the clearance of certain tumors, as well as bacterial, fungal, viral, and parasitic infections. Furthermore, in rare cases of human congenital immune deficiencies, the absence of NK cells produces a clinical spectrum that parallels classical severe combined immunodeficiency (SCID) syndromes. The importance of NK cells is magnified in a host of clinical states in which the adaptive immune system is compromised. These states include congenital immune disorders, iatrogenic immune suppression following organ transplantation, and the Acquired Immune Deficiency Syndrome (AIDS). Natural killer cells represent an attractive target for therapeutic manipulation to fight the rampant opportunistic infections and virus-induced cancers that arise under these states of adaptive immunoparalysis. Indeed, this is the rationale underlying ultra low-dose interleukin-2 therapy to heighten cytokine production and potentiate the anti-tumor effects of NK cells in AIDS-associated malignancies (Fehniger et al., 2002). This approach is further substantiated by recent advances in bone marrow transplantation, in which donor-derived NK have been shown to mediate a potent graft versus tumor effect in acute myeloid leukemia (Ruggeri et al., 2002). In view of these advances, a greater mechanistic understanding of NK cells and the innate immune system is needed for providing new means to enhance the function of these cells for the benefit of the immunocompromised patient.

In order to achieve this level of understanding, it is essential to genetically manipulate NK cells. It is only through such experimentation can one discern the role of specific gene products in the signal transduction pathways that govern NK cell behavior. Up to this point, however, the transfection of genetic material into NK cells has presented a major technical hurdle. While some success has been enjoyed with vaccinia vectors, this technique is limited to short-term experiments, given the lytic nature of poxvirus infections. Moreover, since poxviruses exert a general negative influence on nuclear function, cellular transfection with these vectors severely hampers studies of transcription. More recently, the refinement of electroporation methodologies for NK cells has offered an alternative to viral vectors (Trompeter et al., 2003). However, our own experience with this technology is that it is severely limited by DNA size and choice of DNA vector (B. Becknell, unpublished observations).

Thus, there exists a need in the art for methods for stably transfecting NK cells. The present invention answers that need.

SUMMARY OF THE INVENTION

Features and Advantages of the Invention

This invention presents a novel retrovirus-based method for transfection of human primary natural killer (NK) cells with genetic material. Unlike previous approaches, this technique results in successful transfection of the CD56$^{dim}$ NK population that predominates among human peripheral blood NK and which is the cellular effector of antibody-dependent cellular cytotoxicity (ADCC). The present invention also results in stable transfection of the CD56$^{bright}$ NK subset as well as NK-derived cell lines.

The inventive methodology can be applied to study specific genetic pathways in NK cells and also finds use in the genetic modification of NK cell populations for enhanced therapeutic efficacy in patients with malignancies that are highly susceptible to such immunotherapeutic intervention, including but not limited to, renal cell carcinoma, melanoma, acute myeloid leukemia, and AIDS-related lymphoma.

Up to this point in time, technical hurdles have prevented efficient retroviral transfection of primary NK cells. The advantages of this invention over other methodologies for genetic manipulation of human primary NK cells are summarized by at least the following three points:

(1) This retrovirus-based approach results in the permanent transfection of NK cells with genetic material. This is in contrast to episomal vectors that are lost with cell division/long-term culture and poxvirus vectors that inhibit nuclear function and eventually instigate host cell lysis.

(2) Unlike other retroviral infections of NK cells, the present approach is believed to be the first to result in successful transfection of the CD56$^{dim}$ NK population.

(3) We demonstrate transfection of a variety of genes into primary NK and NK-derived cell lines, with expression of a marker for infection (the green fluorescent protein) as well as the proteins (examples of which are described hereinafter).

Finally, with the advent of NK-cell transplantation in cancer therapy for patients with acute myeloid leukemia, the present genetic manipulation of NK cell populations prior to administration will provide therapeutic benefit for the patient—by enhancing NK cell survival, cytolytic function, cytokine production, and/or tumor specific killing.

Additional features and advantages of the invention will be set forth in part in the description that follows, and in part will be obvious from the description, or may be learned by practice of the invention. The features and advantages of the invention will be realized and attained by means of the elements and combinations particularly pointed out in the appended claims.

SUMMARY OF THE INVENTION

The present invention is directed to a facile, reproducible methodology for retroviral transfection of human primary NK cells. Large cDNAs (up to about 3.8 kilobases (kB) in length) and the green fluorescent protein (GFP, used as a marker of infection) have been simultaneously expressed using the inventive methods. In contrast with other studies reporting retroviral infection of primary NK, the present inventive approach permits the transfection of the CD56$^{dim}$ NK subset that predominates in human peripheral blood.

The invention provides methods for stably transfecting mammalian natural killer cells by: transfecting a packaging cell line with a retroviral expression vector; culturing the transfected packaging cell line in a cell culture medium; and culturing the mammalian natural killer cells with the cell culture medium. In some embodiments, the packaging cell line is chosen from a Phoenix cell line, which can be Phoenix-Ampho. In some embodiments, the retroviral expression vector is PINCO. In some embodiments, the invention further includes separating the transfected packaging cell line from the cell culture medium in which the cell line is cultured prior to culturing the mammalian natural killer cells with the cell culture medium.

The invention also relates to non-naturally occurring mammalian natural killer cells, stably transfected, which express at least one of green fluorescent protein and CD8. The invention is also directed to progeny cell lines of these non-naturally occurring mammalian natural killer cells, wherein the cell line is polyclonal.

The invention also relates to non-naturally occurring mammalian natural killer cell lines, which stably express their genomes through at least two, four, or eight population doublings.

It is to be understood that both the foregoing general description and the following detailed description are exemplary and explanatory only and are not restrictive of the invention, as claimed.

The accompanying drawings, which are incorporated in and constitute a part of this specification, illustrate embodiments of the invention and together with the description, serve to explain the principles of the invention.

BRIEF DESCRIPTION OF THE DRAWINGS

FIG. 1A is a schematic representation of a selection of constructs that were prepared. Frame 1B shows infection of human peripheral blood NK subsets with PINCO. The numbers in the upper right-hand corner of each histogram refer to the percent positive cells per quadrant, after first gating on viable cells. Frame 1C shows RT-PCR for TSC-22R in primary NK transfected with this gene, compared to mock- and vector-only controls, compared to β-actin control reactions. Frame 1D shows PINCO TSC-22R transfected cells before and after enrichment by FACS.

DESCRIPTION OF THE EMBODIMENTS

Figure 1:
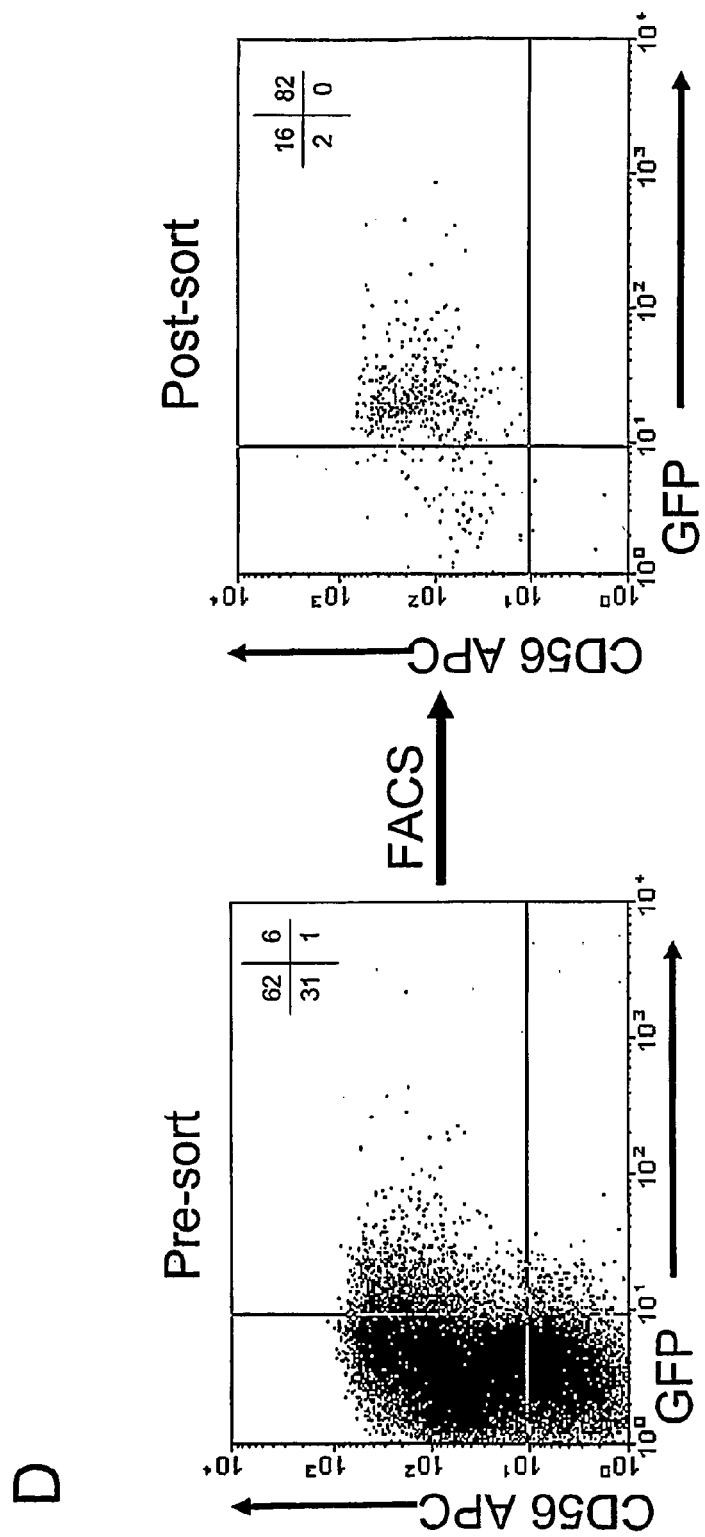
FIG. 1 relates to infection of primary NK cells with PINCO.

Reference will now be made in detail to specific embodiments (exemplary embodiments) of the invention, examples of which are illustrated in the accompanying drawings.

Sequence Listing

The instant application contains a Sequence Listing which has been submitted in ASCII format via EFS-Web and is hereby incorporated by reference in its entirety. Said ASCII copy, created on Feb. 8, 2013, is named 22727.04450_ST25.txt and is 4,096 bytes in size.

The present invention is directed to methods of stably introducing foreign nucleic acids into mammalian cells, including for example, lymphocytic cells. The mammalian cells that can be transformed include, but are not limited to, natural killer cells. Natural killer cells include, but are not limited to, primary NK cells, NK-92, NKL, NK-cell subpopulations, including CD56$^{bright}$ and CD56$^{dim}$ NK cells, and NK-derived cells, which further includes lymphokine-activated killer (LAK) cells, which are cytokine-activated and cytokine-expanded NK cells, and NK clones.

The foreign nucleic acids are introduced into the mammalian cells by a process involving a retroviral expression vector and a packaging cell line. Basically, the foreign nucleic acid is incorporated into the retroviral expression vector, which is then transfected into the packaging cell line, which then allows the vector to propagate. When the mammalian cell line is placed in the presence of the propagated retrovirus, infection occurs, thereby introducing the foreign nucleic acid into the mammalian cell and allowing incorporation of a cDNA encoding the protein of interest into the genome of the cell.

The cDNA can be of any size, and can range, for example, up to 5 kB in length, or even higher. In some embodiments, the cDNA can be smaller, such as 0.5 kB, in some embodiments larger, such as 4 kB. Sizes can range from 0.5 to 5 kB, or 1, 2, 3, 4, or higher kB. The present methods allow for uses of larger cDNAs.

The retroviral expression vectors that can be used in accordance with the present invention include, for example, those based on the Epstein-Barr virus (EBV), which can produce episomal propagation of the retroviral transfer vector. Examples of this type of retroviral expression vectors include, but are not limited to, PINCO, which is described in Grignani et al.

Foreign nucleic acid sequences are introduced into the expression vectors using conventional techniques.

Packaging cell lines that can be used in accordance with the present invention include, but are not limited to, Phoenix packaging cell lines, which further include, but are not limited to, ecotropic (Phoenix-ECO) and amphotropic (Phoenix-Ampho). Other examples include the commercially available BD Biosciences lines, including BD RetroPack, BD AmphoPack, and BD EcoPack, as well as PA317, an NIH 3T3-based, amphotropic, packaging cell line, Apex, derived from ECV304 (human umbilical vein endothelial cell line HUVECS)/T24 (human bladder cell line), BOSC23, which is derived from HEK 293 T-cells, and PG13, which is derived from TK-NIH/3T3 (mouse fibroblast) cells.

The packaging cell lines are infected with the retroviral vector using conventional techniques.

The transfected packaging cell line is cultured until a sufficiently high viral titer is generated. Determination of the sufficiency of the viral titers is well within the level of one of ordinary skill, and the determination can be made empirically. In some embodiments, the transfected packaging cells are cultured for greater than or equal to about 8 hours, or 16 hours, or one day, or two days, or three days or more. The culturing can be maintained until the viral titer reaches $10^4$, $10^5$, $10^6$, $10^7$, or higher.

When a sufficiently high titer is achieved, the mammalian cells can be transfected using the cell culture medium containing the retroviral vector. This process is performed using conventional culture techniques.

Mammalian cell lines transfected according to the present invention are stably transfected. That is, the foreign nucleic acid introduced into the mammalian cell's genome is passed on to progeny cells. Thus, the foreign nucleic acid is present in the first doubled population of NK or NK-derived cells, along with the third, fourth, fifth, etc., to as many as 20 or more doublings. As doubling time may be several days to a week, the foreign nucleic acid will be present in progeny cell lines for more than a week, or two weeks, or three weeks, or one month, or two months, or six months, or one year, or more.

EXAMPLES

Materials and Methods
Generation of Retrovirus and Lentivirus
Generation of PINCO Retrovirus The PINCO retroviral transfer plasmid, originally from the laboratory of Dr. P. G. Pelicci (Grignani et al., 1998), was obtained through the courtesy of Dr. Martin Sattler (Dana Farber Cancer Institute, Boston, Mass.). This retroviral vector permits the expression of a gene of interest from the 5' long term repeat (LTR) as well as GFP from an internal cytomegalovirus (CMV) immediate early promoter. Complementary DNA (cDNA) from genes of interest (including T-BET, TSC-22R, and LDB1; FIG. 1 is a schematic representation of the constructs) ranged in size from 0.5 to 3.8 kB and was cloned into the BamHI and/or EcoRI sites of PINCO. Alternatively, a truncated murine CD8 cDNA was prepared as described in Kinoshita et al. (*Immunity* 6, pp 235+, 1997) and cloned into the HindIII and NotI sites of PINCO, substituting for EGFP cDNA. This construct was termed PINCO8. Following confirmation of cloning by DNA sequencing, each construct was prepared for virus production by endotoxin-free maxiprep (Qiagen, Carlsbad, Calif.). A plasmid expressing the VSV-G protein (pVSV-G) was similarly prepared.

VSV-G pseudotyped retroviral particles were generated by transient transfection of the Phoenix-Ampho packaging line (a gift of Dr. Gary Nolan, Stanford University). Early passage Phoenix cells were cultured (37° C./5% $CO_2$) on T75 flasks in high glucose Dulbecco's Modified Eagle Medium (DMEM) supplemented with GlutaMAX, antibiotic/antimycotic and 10% fetal bovine serum (all from Invitrogen), hereafter denoted D-10. Phoenix cells were transfected at approximately 80% confluence, after having replaced the medium with D-10 containing chloroquine (Sigma) at 25 μM final concentration. Twenty micrograms (μg) of PINCO and 0.9 μg of pVSV-G were cotransfected into Phoenix cells using the PROFECTION® Mammalian Transfection System-Calcium Phosphate (Promega). Transfected cells were cultured for 12-16 hours at 37° C./5% $CO_2$.

Thereafter, the medium was replaced with RPMI supplemented with GlutaMAX, antibiotic/antimycotic, and 20% fetal bovine serum, hereafter denoted RPMI-20. Cells were returned to 37° C./5% $CO_2$ for another 24 hours. Then, virus-containing supernatant was aseptically filtered through 0.45-μm cellulose acetate (Corning) and use immediately or aliquoted and frozen at −80° C.

Transfection of Primary Human NK Cells, NK-Derived Cell Lines, and Other Lymphocyte Populations
Transfection of Primary NK Cells Human peripheral blood leukocytes were obtained as discarded buffy coats from the American Red Cross. NK cells were enriched by rossetting (which is a negative selection strategy using bivalent antibodies simultaneously targeting cells of an unwanted lineage (i.e., T, B, and monocytes) and red blood cells, permitting depletion of these cells upon Ficoll centrifugation; Stem Cell Technologies) and Ficoll-Hypaque density centrifugation. Following removal of monocytes by plastic adherence, the preparation contains $2.5 \times 10^7$ to $1 \times 10^8$ peripheral blood mononuclear cells (PBMC), of which approximately 80% are NK as revealed by flow cytometric analysis of the surface antigens CD56 and CD3 (Human NK cells are $CD56^{bright/dim}CD3^{neg}$). This enriched NK (eNK) preparation was cultured for 48 hours at 37° C./5% $CO_2$ in RPMI-20 supplemented with recombinant human interleukin-2 (IL-2, Roche) at a final concentration of 900 international units (IU)/ml.

Next, between $2 \times 10^6$ to $3 \times 10^6$ eNK were harvested by centrifugation, resuspended in 2 ml viral supernatant supplemented with IL-2 (900 IU/ml) and polybrene (Sigma, 8 ug/ml), and placed in one well of a 6-well tissue-cultured treated plate (Fisher). The plate was centrifuged in a microcarrier bucket at 1800 rpm for 45 minutes at 32° C. (Beckman). Following a 2 hour incubation at 32° C./5% $CO_2$, medium was gently removed by pipetting using a P1000 and replaced with an additional 2 ml of viral supernatant, supplemented as described. The plate was re-centrifuged and returned to 32° C./5% $CO_2$ for another 4 hours. Next, the medium was gently removed and replaced with RPMI-20 containing IL-2 (900 IU/ml), and cells were incubated overnight at 37° C./5% $CO_2$. The following day, medium was gently removed and replaced with 4 ml of viral supernatant, supplemented as described. The plate was centrifuged a third time and returned to 32° C./5% $CO_2$ for 5 hours. Finally, the medium was gently removed and replaced with RPMI-20 containing IL-2 (150 IU/ml), and cells were cultured from this point onwards at 37° C./5% $CO_2$.

Transfection of IL-2/KL Expanded Primary $CD56^{bright}$ NK Cells

To transfect the $CD56^{bright}$ NK subset, eNK were seeded at $10^6$/ml in RPMI supplemented with antibiotic/antimycotic, GlutaMAX, and 10% human AB serum (ICN), supplemented with IL-2 at 150 IU/ml and c-kit ligand (KL, Amgen) at 100 ng/ml final concentration.

Transfection of NK-Derived Cell Lines

The NK-92 cell line was obtained from Dr. Hans Klingemann, Rush Medical Center. The NKL cell line was obtained from Drs. Michael Robertson (Indiana University) and Jerome Ritz (Harvard University). Both lines were cultured in RPMI-20 supplemented with IL-2 (Roche, 150 IU/ml) at 37° C./5% $CO_2$. On the day before infection, IL-2 concentration was adjusted to 900 IU/ml. The infections were performed as described in Section A. Following the final round of infection, the IL-2 concentration was returned to 150 IU/ml.

Use of CD8 as a Sorting Facilitator ("PINCO8")

Rather than use GFP as a marker for NK transfection, we have substituted a modified mouse CD8 mRNA, which encodes a cytoplasmically truncated protein that is targeted to the cell membrane but which lacks signaling properties, rendering this molecule inert. Since the extracellular domain of the CD8 is preserved, transfected NK-92 were detected by flow cytometry using well-established monoclonal antibodies to this molecule, which are conjugated to fluorescence molecules. The use of CD8 and GFP in separate viruses permits infection of NK cells with more than one gene. Furthermore, the use of CD8 allows the possibility to isolate transfected cells using magnetic beads pre-conjugated to anti-CD8, eliminating the need to rely on fluorescence-assisted cell sorting (FACS) for purification of the transfected population.

Analysis of Transfected NK Cells

Expression of TSC-22R was detected by RT-PCR using AmpliTaq Gold (Applied Biosystems), forward (5'-ACCAGCTGCACAATTTCTCC-3') SEQ ID NO. 1, reverse (5'-TACACCGCAGAACCACCAG-3') SEQ ID NO. 2, and the following conditions: 94° C. 10 min; followed by 25 cycles of 94° C. 30 sec, 60° C. 30 sec, 72° C. 1 min. Parallel reactions were performed using primers to the housekeeping gene, β-actin: forward (5'-GGAATCGTGCGTGACATTAAG-3') SEQ ID NO. 3, and reverse (5'-TGTGTTGGCGTACAGGTCTTTG-3') SEQ ID NO. 4. Expression of proteins of interest was confirmed by immunoblotting for a C-terminal MYC epitope (Cell Signaling) or other terminal epitopes, as described (in Trotta et al., 2003, Cancer Cell 3, pp. 145+). Subsequent functional analysis of cytokine production (ELISA, intracellular staining) and cytotoxicity (51Cr-release) was performed exactly as previously described (in Carson et al., 1994, J. Exp. Med. 180, pp. 1395+; and in Cooper et al., 2001, Blood 97, pp. 3146+).

Expression of TSC-22R was detected by RT-PCR using AmpliTaq Gold (Applied Biosystems), forward (5'-ACCAGCTGCACAATTTCTCC-3'), reverse (5'-TACACCGCAGAACCACCAG-3'), and the following conditions: 94° C. 10 min; followed by 25 cycles of 94° C. 30 sec, 60° C. 30 sec, 72° C. 1 min. Parallel reactions were performed using primers to the housekeeping gene, β-actin: forward (5'-GGAATCGTGCGTGACATTAAG-3') and reverse (5'-TGTGTTGGCGTACAGGTCTTTG-3'). Expression of proteins of interest was confirmed by immunoblotting for a C-terminal MYC epitope (Cell Signaling) or other terminal epitopes, as described (in Trotta et al., 2003, Cancer Cell 3, pp. 145+). Subsequent functional analysis of cytokine production (ELISA, intracellular staining) and cytotoxicity ($^{51}$Cr-release) was performed exactly as previously described (in Carson et al., 1994, J. Exp. Med. 180, pp. 1395+; and in Cooper et al., 2001, Blood 97, pp. 3146+).

Results

Transfection of Primary NK Cells

To determine if PINCO could infect primary NK cells, multiple infections were performed on enriched NK preparations from human peripheral blood, with vector alone or with vector bearing various genes of interest, over a 48-hour period. The results were visualized cytometrically by EGFP fluorescence, compared to mock-infected controls.

FIG. 1A schematically illustrates selected vectors described herein. As shown with TSC-22R in FIG. 1B, PINCO is capable of transfecting both $CD56^{bright}$ and $CD56^{dim}$ subsets. In addition, the overexpression of TSC-22R mRNA is evident by RT-PCR analysis compared to vector-only and mock-infected controls (FIG. 1C). Thus, PINCO is capable of delivering multiple genes (i.e., EGFP and TSC-22R, for example) to primary NK cells. Following NK cell infections, the $CD56^+GFP^+$ cells were enriched by FACS (FIG. 1D).

Figure 2:
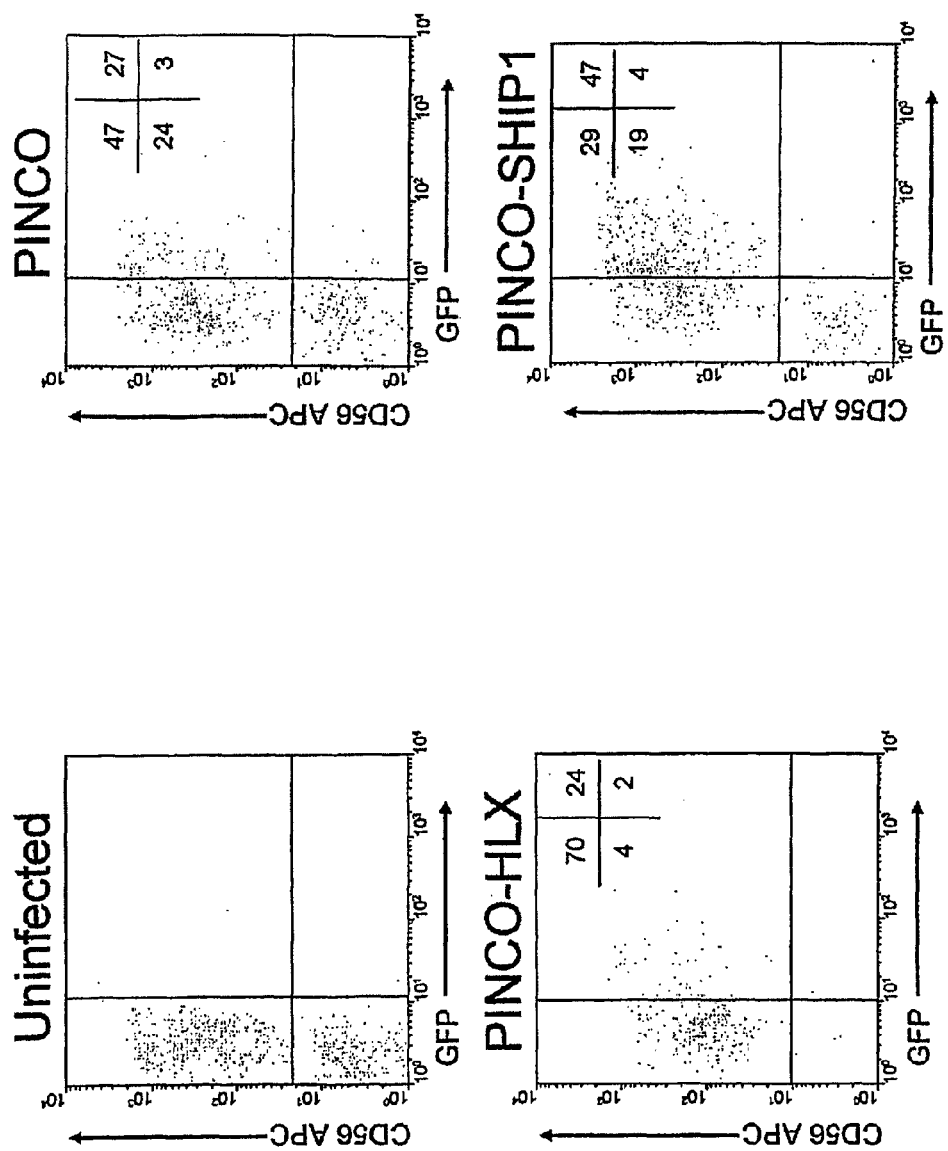
FIG. 2 demonstrates infection of primary natural killer cells with PINCO, PINCO-HLX (1.5 kb cDNA) and PINCO-SHIP1 (3.8 kb cDNA), evaluated by flow cytometry. Numbers in the crosshairs indicate percentage of events for each quadrant.

FIG. 2 illustrates multiple eNK infections performed and visualized cytometrically by EGFP fluorescence. To the best of our knowledge, there are only two other reports documenting retroviral transfection of primary NK cells in the scientific literature (Chiorean et al., 2003; Unutmaz et al., 1999). However, these infections—using MSCV-based retrovirus (Chiorean et al., 2003) or HIV-based lentivirus (Unutmaz et al., 1999)—were limited in efficacy to the $CD56^{bright}$ NK subset. In contrast, the present approach using PINCO is broadly applicable to all NK cells, i.e., $CD56^{bright}$ NK, as well as the $CD56^{dim}$ NK subset that predominates in human peripheral blood (Cooper et al., 2001). Furthermore, as shown in FIG. 2, the present invention transfected cDNAs up to 3.8 kB in size, with no decrease in viral titer or NK transfection.

Transfection of IL-2/KL Expanded Primary $CD56^{bright}$ NK Cells

Figure 3:
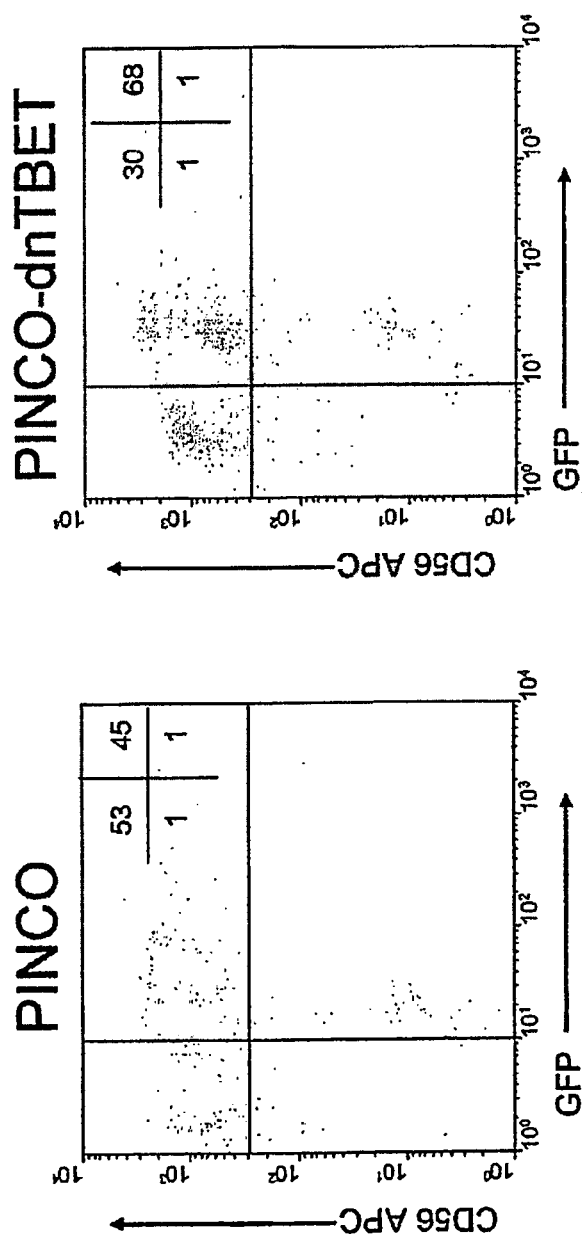
FIG. 3 demonstrates infection of primary IL-2/KL expanded CD56bright natural killer cells with PINCO and PINCO-dnTBET (2.0 kb cDNA), evaluated by flow cytometry. Numbers in the crosshairs indicate percentage of events for each quadrant.

Following 1-week incubation at 37° C./5% $CO_2$, cells typically expanded 3-4 fold. Whereas peripheral blood NK typically comprises two major subsets, $CD56^{bright}$ (5-15% of NK) and $CD56^{dim}$ (85-95% of NK), this weeklong culture in IL-2 and KL enriches massively for the $CD56^{bright}$ subset, to the point that it represents 90% or more of the total cell number. Between $1-5 \times 10^6$ IL-2/KL expanded NK were transfected with PINCO as described above, except that KL was included throughout the infection period at 100 ng/ml final concentration. This reproducibly resulted in profoundly high levels of infection, as illustrated in FIG. 3.

Transfection of NK-Derived Cell Lines

Figure 4:
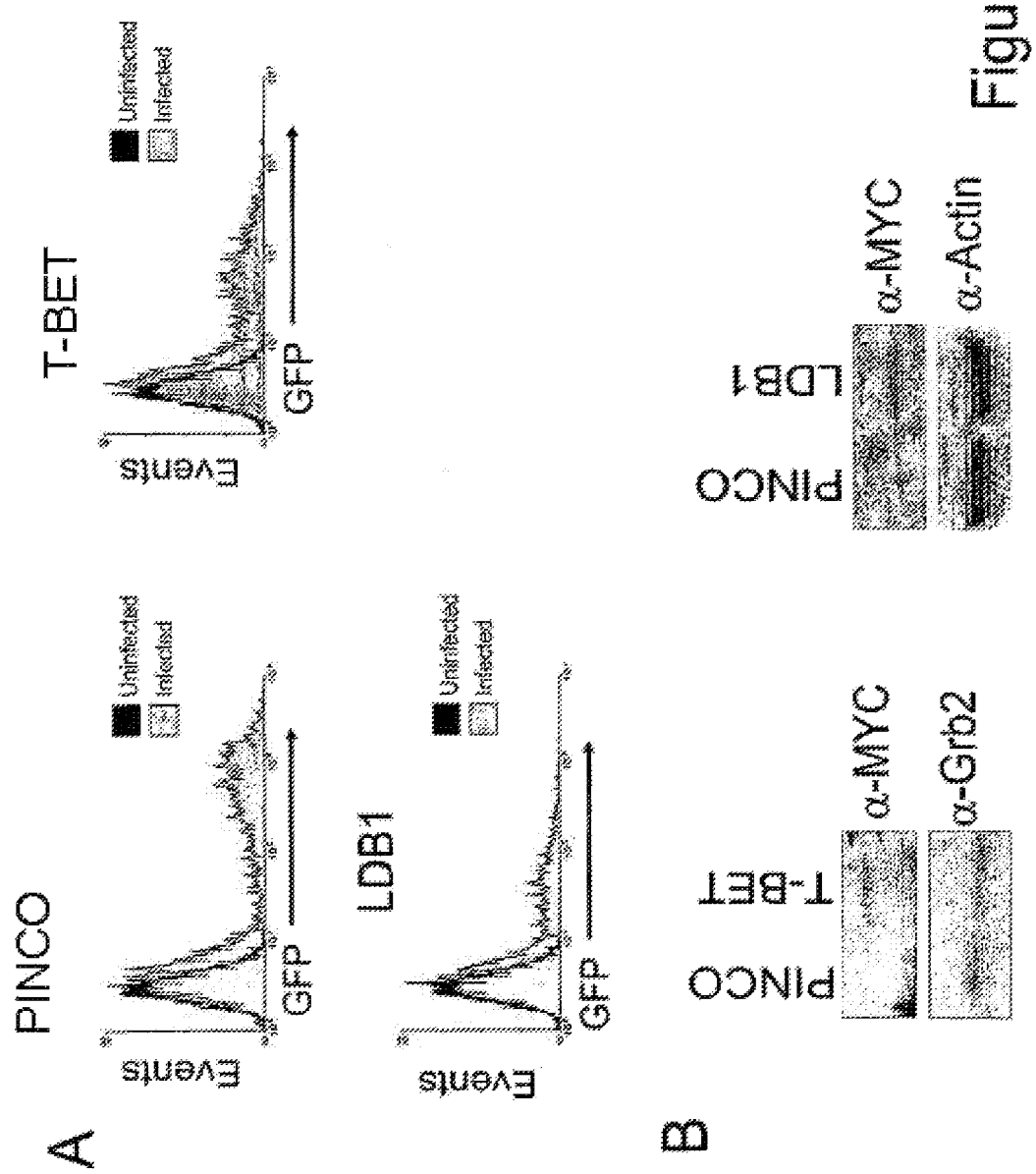
FIG. 4 relates to infection of human NK-92 cells with PINCO. Frame 4A shows NK-92 cells infected with T-BET, LDB1, and empty PINCO virus. Frame 4B shows retrovirus-mediated protein expression revealed by Western blotting for a MYC epitope. Filters were reprobed for β-actin or Grb2 to demonstrate equal loading.

The human cell line, NK-92, serves as an excellent model for the $CD56^{bright}$ NK subset, as NK-92 cells are capable of robust INF-γ production upon stimulation with combinations of monokines, such as IL-12, IL-15, and IL-18 (Strengell et al., 2003, J. Immunol. 170, pp 5464+). Thus, it was sought to determine if PINCO is capable of infecting NK-92 cells. As shown for T-BET and LDB1 in FIG. 4A, the NK-92 cell line was successfully infected with PINCO bearing multiple genes of interest. GFP(+) NK-92 cells have been isolated to $\geq 99\%$ purity by FACS and been maintained in culture for over 3 months, with no appreciable reduction in GFP fluorescence. To confirm the expression of proteins of interest in the NK-92 cells, immunoblotting was performed to detect a C-terminal MYC epitope (FIG. 4B).

Figure 5:
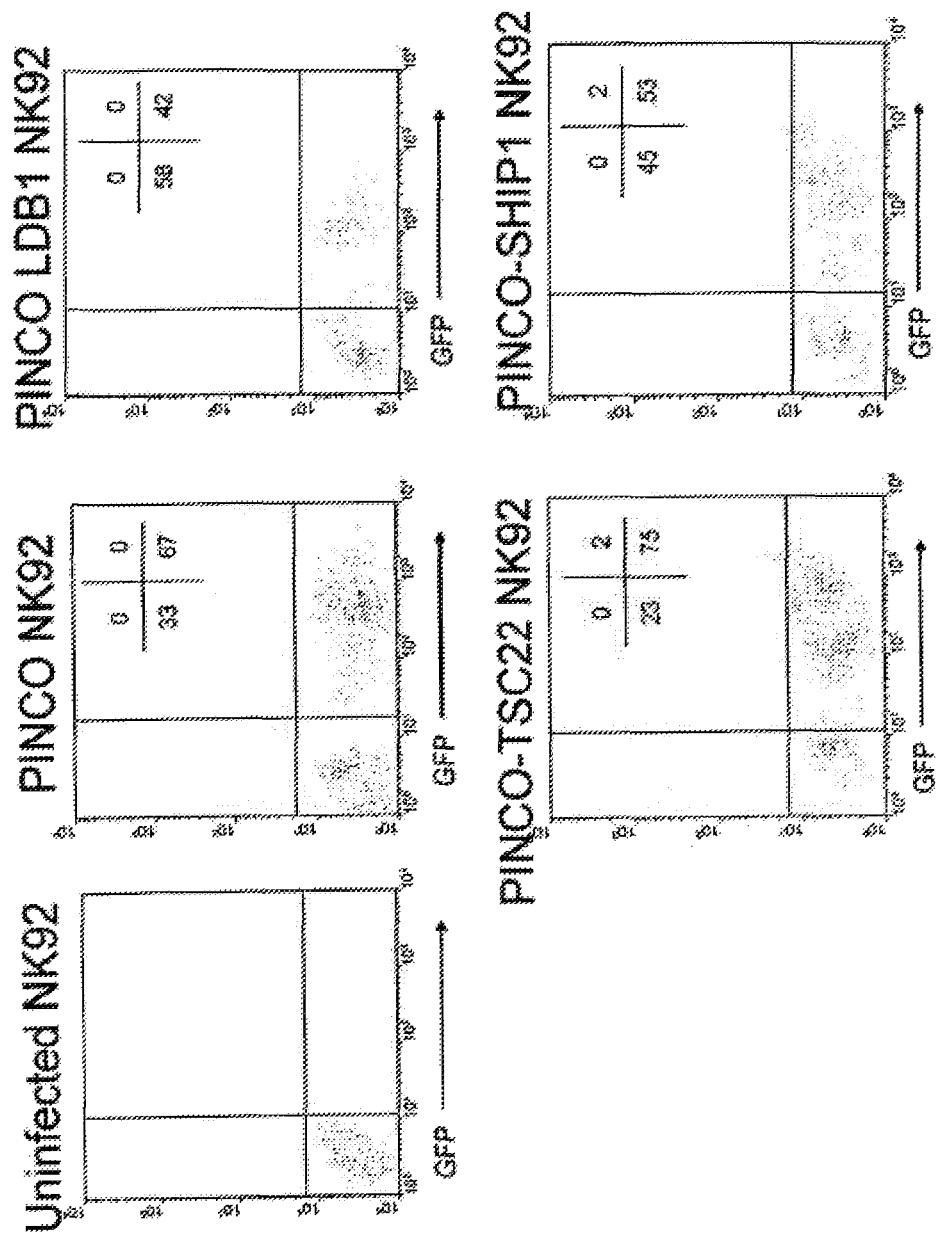
FIG. 5 demonstrates infection of the NK-92 cell line with PINCO, PINCO-dnTBET (2.0 kb cDNA), PINCO-LDB1 (1.1 kB cDNA), PINCO-TSC22 (0.5 kB cDNA), and PINCO-SHIP1 (3.8 kB cDNA), evaluated by flow cytometry.
Figure 6:
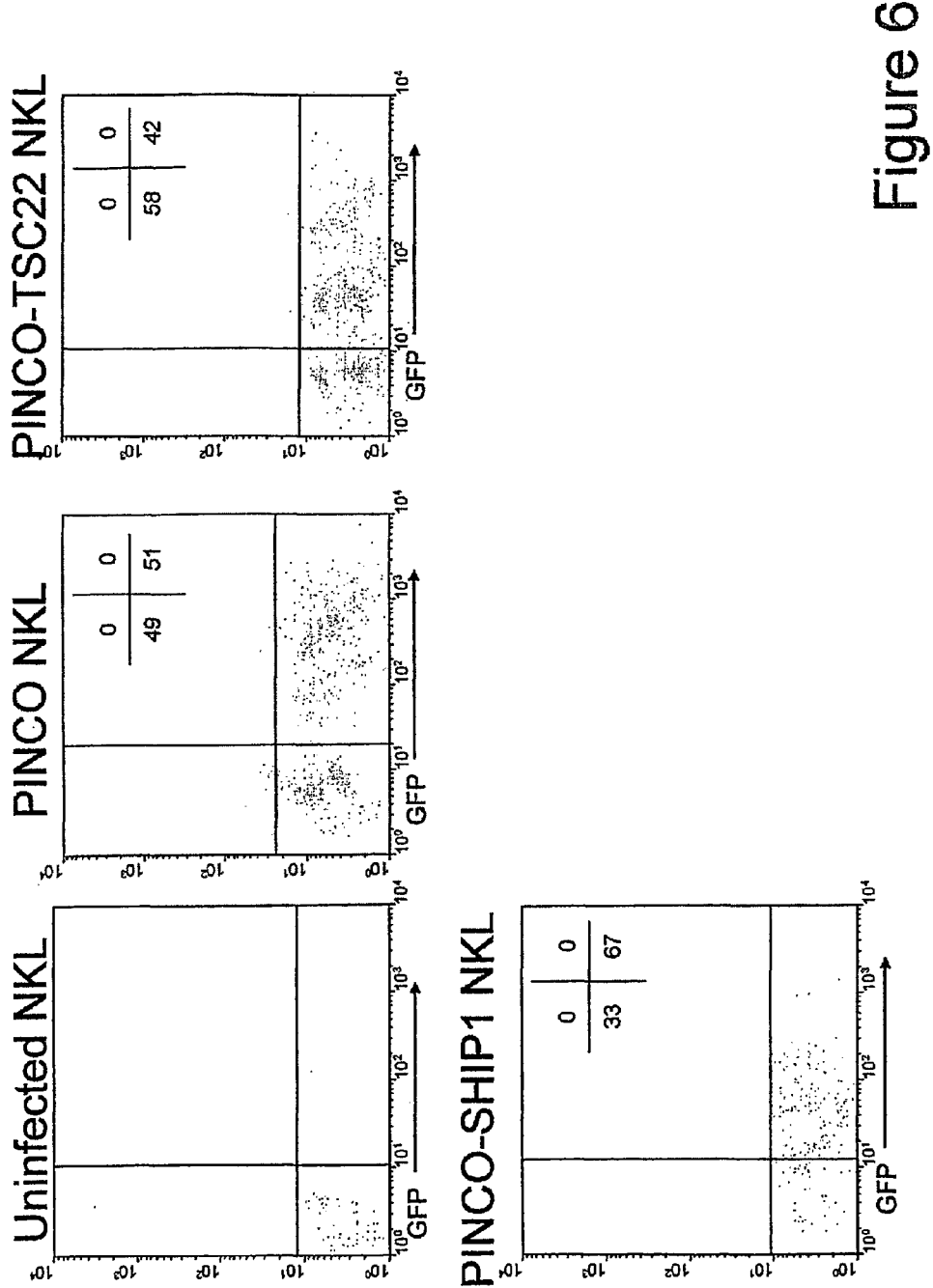
FIG. 6 demonstrates infection of the NKL cell line with PINCO, PINCO-TSC22 (0.5 kb cDNA), and PINCO-SHIP1 (3.8 kB cDNA), evaluated by flow cytometry.
Figure 7:
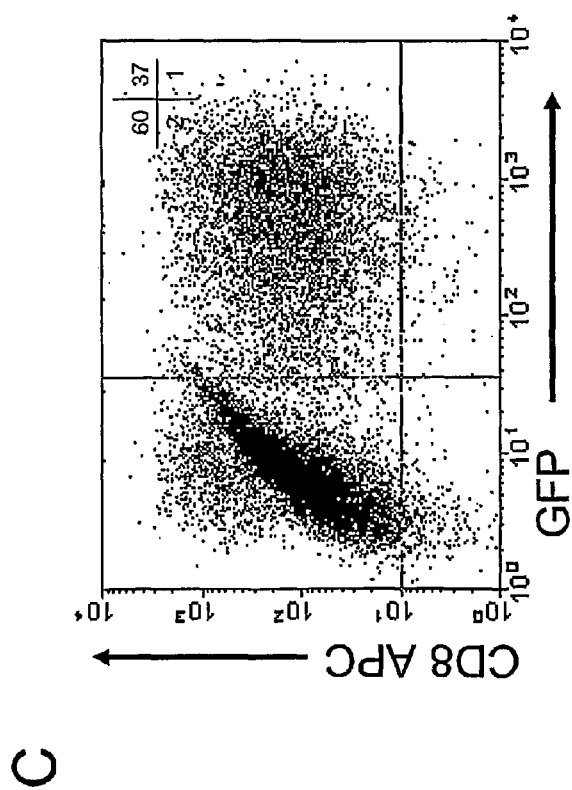
FIG. 7 relates to infection of NK-92 cells with PINCO8. Frame 7A schematically illustrates substitution of a truncated murine CD8 cDNA for EGFP, yielding the PINCO8 construct. Frame B shows magnetic selection of PINCO8-infected NK-92 cells. FIG. C shows simultaneous transfection of NK-92 cells with PINCO and PINCO8, as revealed by CD8(+)EGFP(+) cells on cytometric analysis.

High levels of infection were not only achieved for NK-92, as shown in FIG. 5, but also for human NKL cells, as shown in FIG. 6. Similar results have been reported in the scientific literature (Chiorean et al., 2003; Kikuchi-Maki et al., 2003), using MSCV-based transfer vectors. To the best of our knowledge, however, this is the first report of PINCO's use as a gene delivery vector for primary NK cells.

Infection of NK-92 Cells with PINCO8

Figure 8:
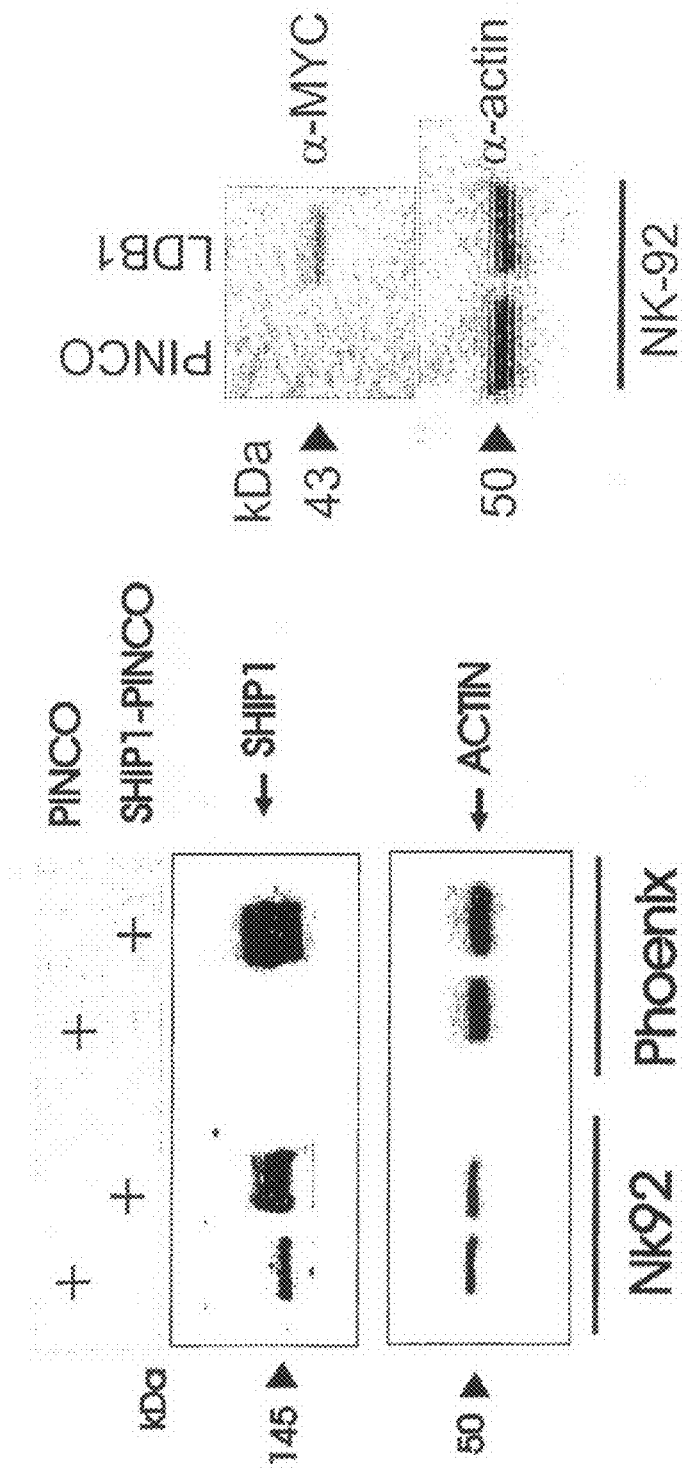
FIG. 8 shows Western blot analysis of FACS purified, virally transfected NK cell lines confirms overexpression of proteins of interest (SHIP, On the left, and LDB1, on the right).

In order to increase the versatility of the vector, PINCO was modified to express a cytoplasmically truncated murine CD8 molecule in place of GFP. The resulting vector, shown schematically in FIG. 8A, is termed PINCO8. As an alternative to purification of transfected NK populations by FACS, PINCO8 transfected NK-92 cells were stained with anti-mouse CD8 PE followed by anti-PE magnetic beads. After two rounds of magnetic selection, ≧95% pure population of CD8(+) cells were routinely observed (FIG. 8B). NK-92 cells were next simultaneously infected with PINCO and PINCO8, which revealed a GFP(+)CD8(+) population on subsequent cytometric analysis (FIG. 8C). Thus, NK-92 cells can be infected with multiple PINCO retroviruses, each carrying unique genetic material.

Further Analysis

Figure 9:
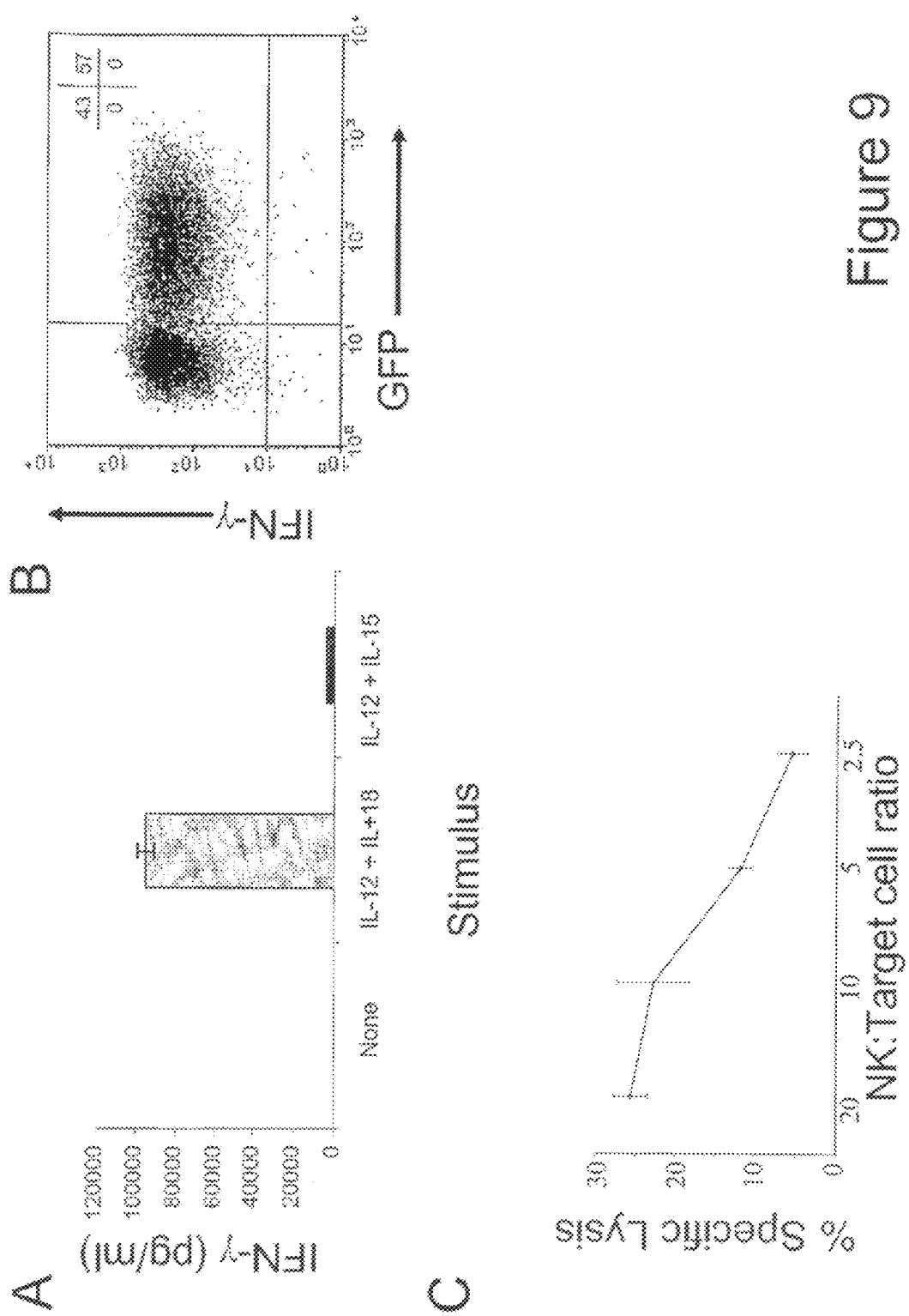
FIG. 9 relates to the ability of infected NK and NK-92 cells to retain NK effector functions. Frame A shows that FACS-purified, infected primary NK cells are capable of IFN-γ production in response to monokine stimulation as revealed by ELISA. Frame B shows intracellular staining for IFN-γ production by FACS-sorted, PINCO-infected NK-92 in response to IL-12 plus IL-18 stimulation, compared to isotype control. Frame C shows that, upon FACS purification, infected NK-92 cells exhibit cytolytic activity toward C7M3 targets in a $^{51}$Cr-release assay.

Following retroviral infection of primary NK and NK-derived cell lines, the transfected populations were routinely isolated to >99% purity by fluorescence-assisted cell sorting (FACS) for GFP$^+$ cells. When virally transfected NK-92 and NKL were subjected to long-term culture (>3 months), no significant decrease in GFP fluorescence was observed. As an alternative to GFP, expression of proteins of interest was monitored directly by immunoblotting. Indeed, Western blot analysis of FACS purified, virally transfected NK cell lines reveals significant overexpression of these proteins, as shown in FIG. 9.

Further analysis was performed to determine the level to which retrovirally transfected cells maintained the NK effector functions of cytokine production and cytolytic activity. After FACS purification, primary NK cells are capable of IFN-γ production in response to monokine stimulation, as shown by ELISA (FIG. 10A). Similarly, retrovirally infected NK-92 cells produce high levels of IFN-γ in response to monokine treatment, as shown both by intracellular staining (FIG. 10B) and ELISA (data not shown). Virally transfected cells also exhibit cytolytic activity in $^{51}$Cr-release assays (FIG. 10C). Thus, transfection of NK and/or NK-92 cells with PINCO retrovirus preserves cellular functions, including cytolysis and cytokine elaboration.

These technical advances pave the way for mechanistic studies of the roles of individual genes in NK cell function. In addition, with the advent of NK-cell transplantation in cancer therapy for patients with acute myeloid leukemia, the genetic manipulation of NK cell populations prior to administration may conceivably provide therapeutic benefit for the patient—by enhancing NK-cell survival, cytolytic function, cytokine production, and/or tumor-specific killing.

V. RNAi Example

RNA interference (RNAi) is a method for silencing expression of specific gene(s) of interest based on the transfection of small, double-stranded RNA sequences identical to the mRNA of the particular gene(s). We modified PINCO to express a CD8 along with an RNAi cassette from the pSUPER plasmid (OligoEngine, Seattle, Wash.), which was previously engineered to express a short hairpin RNA (shRNA) that targets a specific gene, T-BET. Transfection of NK cells results in the expression of CD8 (as a marker of infection) and the shRNA from separate promoters. The shRNA, which contains complementary regions to permit folding on itself to form a hairpin, is subsequently processed by cellular enzymes to form a double-stranded RNA that targets and silences the gene of interest.

VI. Citations

Chiorean E G, Dylla S J, Olsen K, Lenvik T, Soignier Y, Miller J S. BCR/ABL alters the function of NK cells and the acquisition of killer immunoglobulin-like receptors (KIRs). Blood. 2003 May 1; 101(9):3527-33.

Cooper M A, Fehniger T A, Turner S C, Chen K S, Ghaheri B A, Ghayur T, Carson W E, Caligiuri M A. Human natural killer cells: a unique innate immunoregulatory role for the CD56(bright) subset. Blood. 2001 May 15; 97(10):3146-51.

Fehniger T A, Cooper M A, Caligiuri M A. Interleukin-2 and interleukin-15: immunotherapy for cancer. Cytokine Growth Factor Rev. 2002 April; 13(2):169-83.

Grignani F, Kinsella T, Mencarelli A, Valtieri M, Riganelli D, Grignani F, Lanfrancone L, Peschle C, Nolan G P, Pelicci P G. High-efficiency gene transfer and selection of human hematopoietic progenitor cells with a hybrid EBV/retroviral vector expressing the green fluorescence protein. Cancer Res. 1998 Jan. 1; 58(1):14-9.

Introna M, Barbui A M, Golay J, Bambacioni F, Schiro R, Bemasconi S, Breviario F, Erba E, Borleri G, Barbui T, Biondi A, Rambaldi A. Rapid retroviral infection of human hemopoietic cells of different lineages: efficient transfer in fresh T cells. Br J. Haematol. 1998 November; 103(2):449-61.

Kikuchi-Maki A, Yusa S, Catina T L, Campbell K S. KIR2DL4 is an IL-2-regulated NK cell receptor that exhibits limited expression in humans but triggers strong IFN-gamma production. J Immunol. 2003 Oct. 1; 171(7):3415-25.

M. Sattler, S. Verma, C. H. Byrne, G. Shrikhande, T. Winkler, P. A. Algate, L. R. Rohrschneider, and J. D. Griffin. BCR/ABL Directly inhibits Expression of SHIP, an SH2-Containing Polyinositol-5-Phosphatase involved in the Regulation of Hematopoiesis. Mol. Cell. Biol., Nov. 1, 1999; 19(11): 7473-7480.

Ruggeri L, Capanni M, Urbani E, Perruccio K, Shlomchik W D, Tosti A, Posati S, Rogaia D, Frassoni F, Aversa F, Martelli M F, Velardi A. Effectiveness of donor natural killer cell alloreactivity in mismatched hematopoietic transplants. Science. 2002 Mar. 15; 295(5562):2097-100.

Trompeter H I, Weinhold S, Thiel C, Wernet P, Uhrberg M. Rapid and highly efficient gene transfer into natural killer cells by nucleofection. J Immunol Methods. 2003 Mar. 1; 274(1-2):245-56.

Unutmaz D, KewalRamani V N, Marmon S, Littman D R. Cytokine signals are sufficient for HIV-1 infection of resting human T lymphocytes. J Exp Med. 1999 Jun. 7; 189 (11):1735-46.

Except where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

The specification is most thoroughly understood in light of the teachings of the references cited within the specification, all of which are hereby incorporated by reference in their entirety. The embodiments within the specification provide an illustration of embodiments of the invention and should not be construed to limit the scope of the invention. The skilled artisan recognizes that many other embodiments are encompassed by the claimed invention and that it is intended that the specification and examples be considered as exemplary only, with a true scope and spirit of the invention being indicated by the following claims.

What is claimed is:

1. A method for stably transfecting mammalian primary natural killer cells comprising:
   transfecting a Phoenix cell line with a retroviral expression vector;
   culturing the transfected Phoenix cell line in a cell culture medium;
   and culturing the mammalian natural killer cells with the cell culture medium;
   wherein the transfected mammalian natural killer cells include both $CD56^{bright}$ and $CD56^{dim}$ cell subsets; and
   wherein the transfected mammalian natural killer cells express an exogenous gene for at least two population doublings.

2. The method according to claim 1, wherein the Phoenix cell line is Phoenix-Ampho.

3. The method according to claim 1, wherein the retroviral expression vector is an Epstein-Barr viral vector.

4. The method according to claim 1, further comprising separating the transfected Phoenix cell line from the cell culture medium in which the cell line is cultured prior to culturing the mammalian natural killer cells with the cell culture medium.

5. The method according to claim 1, wherein the vector comprises cDNA of greater than about 2 kB.

6. The method according to claim 5, wherein the vector comprises cDNA of greater than about 3 kB.

7. The method according to claim 6, wherein the vector comprises cDNA of greater than or equal to about 3.8 kB.

8. The method according to claim 7, wherein the vector comprises cDNA of greater than about 4 kB.

9. A non-naturally occurring mammalian CD56$^{dim}$ natural killer cell which expresses an exogenous protein of interest and at least one of green fluorescent protein and CD8.

10. A progeny cell line of the non-naturally occurring mammalian natural killer cell according to claim 9.

* * * * *

```
                       SEQUENCE LISTING

<160> NUMBER OF SEQ ID NOS: 4

<210> SEQ ID NO 1
<211> LENGTH: 20
<212> TYPE: DNA
<213> ORGANISM: artificial
<220> FEATURE:
<223> OTHER INFORMATION: created for mouse

<400> SEQUENCE: 1
accagctgca caatttctcc                                              20

<210> SEQ ID NO 2
<211> LENGTH: 19
<212> TYPE: DNA
<213> ORGANISM: artificial
<220> FEATURE:
<223> OTHER INFORMATION: created for mouse (reverse)

<400> SEQUENCE: 2
tacaccgcag aaccaccag                                               19

<210> SEQ ID NO 3
<211> LENGTH: 21
<212> TYPE: DNA
<213> ORGANISM: artificial
<220> FEATURE:
<223> OTHER INFORMATION: created for mouse (beta-actin forward)

<400> SEQUENCE: 3
ggaatcgtgc gtgacattaa g                                            21

<210> SEQ ID NO 4
<211> LENGTH: 22
<212> TYPE: DNA
<213> ORGANISM: Artificial Sequence
<220> FEATURE:
<223> OTHER INFORMATION: created for mouse (beta-actin reverse)

<400> SEQUENCE: 4
tgtgttggcg tacaggtctt tg                                           22
```